(12) United States Patent
Fujii

(10) Patent No.: US 12,722,025 B2
(45) Date of Patent: Sep. 1, 2026

(54) RADIOTHERAPY DEVICE COMPRISING A POSITIONING DEVICE, AND POSITIONING METHOD

(71) Applicant: Hitachi High-Tech Corporation, Tokyo (JP)

(72) Inventor: Takaaki Fujii, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 217 days.

(21) Appl. No.: 18/695,208

(22) PCT Filed: Jan. 27, 2023

(86) PCT No.: PCT/JP2023/002740
§ 371 (c)(1),
(2) Date: Mar. 25, 2024

(87) PCT Pub. No.: WO2023/157616
PCT Pub. Date: Aug. 24, 2023

(65) Prior Publication Data

US 2024/0390701 A1 Nov. 28, 2024

(30) Foreign Application Priority Data

Feb. 18, 2022 (JP) ................................ 2022-023707

(51) Int. Cl.
*A61N 5/10* (2006.01)

(52) U.S. Cl.
CPC ............. *A61N 5/1069* (2013.01); *A61N 5/10* (2013.01); *A61N 5/1049* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 5,901,199 A * 5/1999 Murphy ................. A61B 6/583
378/65
6,516,046 B1 * 2/2003 Fröhlich .................. A61B 5/70
378/68
(Continued)

FOREIGN PATENT DOCUMENTS

JP 2013-99431 A 5/2013
JP 2016-59606 A 4/2016
(Continued)

OTHER PUBLICATIONS

International Search Report of PCT/JP2023/002740 dated Mar. 14, 2023.
(Continued)

*Primary Examiner* — Allen C. Ho
(74) *Attorney, Agent, or Firm* — MATTINGLY & MALUR, PC

(57) ABSTRACT

A positioning device, a radiotherapy device, and a positioning method enable accurate patient positioning while reducing calculation time. A plurality of X-ray fluoroscopic images are obtained by imaging a subject. For each imaging axis of the X-ray fluoroscopic image, a simulated fluoroscopic image obtained by projecting a three-dimensional fluoroscopic image of the subject onto the detection surface with respect to the imaging axis is created. For each of the plurality of imaging axes, the image collation part obtains a correction axis obtained by correcting the imaging axis based on a two-dimensional motion amount, which is a deviation amount between the X-ray fluoroscopic image and the simulated-X-ray fluoroscopic image corresponding to the imaging axis, and calculates, as a treatment-couch motion amount by which the treatment-couch is to be moved, a motion amount from an intersection of the imaging
(Continued)

axes to a midpoint of a common perpendicular of the correction axes.

9 Claims, 4 Drawing Sheets

(52) U.S. Cl.
CPC .... *A61N 5/1081* (2013.01); *A61N 2005/1061* (2013.01); *A61N 2005/1062* (2013.01); *A61N 2005/1074* (2013.01); *A61N 2005/1087* (2013.01)

(58) Field of Classification Search
CPC .. A61N 5/1043; A61N 5/1045; A61N 5/1047; A61N 5/1048; A61N 5/1049; A61N 2005/1054; A61N 2005/1061; A61N 2005/1062; A61N 5/1064; A61N 5/1065; A61N 5/1067; A61N 5/1068; A61N 5/1069; A61N 5/107; A61N 2005/1074; A61N 5/1081; A61N 2005/1087
USPC .......................................................... 378/62, 65
See application file for complete search history.

(56) References Cited

U.S. PATENT DOCUMENTS 6,674,833 B2 * 1/2004 Shahidi .................. A61B 90/36 378/94
6,714,810 B2 * 3/2004 Grzeszczuk ............. A61B 6/12 606/130
6,865,253 B2 * 3/2005 Blumhofer ............. A61B 6/547 378/65
6,907,281 B2 * 6/2005 Grzeszczuk ........... A61B 90/36 600/407
7,010,080 B2 * 3/2006 Mitschke ............. A61B 6/5235 378/15
7,187,792 B2 * 3/2007 Fu ............................ G06T 7/32 382/128
7,231,076 B2 * 6/2007 Fu ........................... G06T 7/238 382/294
7,260,426 B2 * 8/2007 Schweikard ........... A61B 34/20 600/595
7,302,033 B2 * 11/2007 Carrano ............... A61N 5/1049 378/41
7,315,636 B2 * 1/2008 Kuduvalli ............. G06T 11/008 382/280
7,327,865 B2 * 2/2008 Fu .......................... G06V 10/24 382/128
7,330,578 B2 * 2/2008 Wang ...................... G06T 15/08 345/419
7,366,278 B2 * 4/2008 Fu ......................... G06T 11/008 378/4
7,415,095 B2 * 8/2008 Wofford ................. A61N 5/103 378/65
7,418,079 B2 * 8/2008 Schildkraut .......... A61N 5/1049 378/65
7,426,318 B2 * 9/2008 Fu ........................... G06T 7/344 382/294
7,436,928 B2 * 10/2008 Urano .................. A61N 5/1049 378/65
7,453,984 B2 * 11/2008 Chen .................... A61N 5/1049 378/92
7,522,779 B2 * 4/2009 Fu ........................ A61N 5/1049 382/167
7,620,144 B2 * 11/2009 Bodduluri ............ A61N 5/1049 378/65
7,623,623 B2 * 11/2009 Raanes ................ A61N 5/1049 378/68
7,684,647 B2 * 3/2010 Fu ........................ A61B 6/4458 348/580
7,831,073 B2 * 11/2010 Fu ........................ A61N 5/1049 382/128
7,835,500 B2 * 11/2010 Fu ........................ A61B 6/4458 378/128
8,471,222 B2 * 6/2013 Handa .................. A61N 5/1069 378/65
8,559,596 B2 * 10/2013 Thomson ............. A61N 5/1049 378/65
8,824,630 B2 * 9/2014 Maurer, Jr. .......... A61N 5/1037 378/68
8,831,706 B2 * 9/2014 Fu ........................ A61N 5/1049 378/65
8,874,187 B2 * 10/2014 Thomson ............. A61N 5/1049 378/65
8,917,813 B2 * 12/2014 Maurer, Jr. .......... A61N 5/1049 378/65
8,965,096 B2 * 2/2015 Yamada ............... A61N 5/1049 378/62
9,393,445 B2 * 7/2016 Yamada ............... A61N 5/1049
9,514,538 B2 * 12/2016 Ebisawa ................ A61B 3/113
9,616,249 B2 * 4/2017 Miyamoto ........... A61N 5/1049
9,830,718 B2 * 11/2017 Hirai ...................... A61N 5/107
10,016,625 B2 * 7/2018 Taguchi ............... A61N 5/1049
10,065,049 B2 * 9/2018 Lugosi ................. A61N 5/1049
10,342,996 B2 * 7/2019 Jordan ................. A61N 5/1039
10,532,224 B2 * 1/2020 Jordan ................. A61N 5/1039
10,713,801 B2 * 7/2020 Jordan ................. A61N 5/1049
10,722,733 B2 * 7/2020 Takahashi ............ A61N 5/1049
10,737,117 B2 * 8/2020 Mori .................... A61N 5/1049
10,751,014 B2 * 8/2020 Naylor ................. A61N 5/1049
10,769,467 B2 * 9/2020 Hirai .................... A61N 5/1049
10,813,205 B2 * 10/2020 Jordan ................. A61N 5/1049
10,835,762 B2 * 11/2020 Mori .................... A61N 5/1049
10,918,885 B2 * 2/2021 Haas .................... A61N 5/1037
10,940,331 B2 * 3/2021 Mori .................... A61N 5/1049
10,952,695 B2 * 3/2021 Mori .................... A61N 5/1049
11,049,252 B2 * 6/2021 Miyazaki ............. A61N 5/1049
11,097,129 B2 * 8/2021 Sakata ................. A61N 5/1049
11,278,743 B1 * 3/2022 Frederick ............. A61N 5/1049
11,439,848 B2 * 9/2022 Fujii .................... A61N 5/1067
11,446,520 B2 * 9/2022 Fujii .................... A61N 5/1048
11,478,662 B2 * 10/2022 Sayeh .................. A61N 5/1049
11,660,471 B2 * 5/2023 Miyazaki ............. A61N 5/1077 600/1
11,712,582 B2 * 8/2023 Miyazaki ............. A61N 5/1049 378/65
12,059,579 B2 * 8/2024 Karasawa ............ A61N 5/1049
12,128,252 B2 * 10/2024 Jordan ................. A61N 5/1045
12,165,321 B2 * 12/2024 Sakata ...................... A61N 5/10
12,257,455 B2 * 3/2025 Thompson ........... A61N 5/1049
12,364,877 B2 * 7/2025 Hirai .................... A61N 5/1049
12,605,566 B2 * 4/2026 Hirai .................... A61N 5/1049
2015/0287206 A1 10/2015 Ebisawa et al.
2017/0291042 A1 10/2017 Takahashi
2019/0143146 A1 5/2019 Fujii et al.
2020/0009404 A1 1/2020 Fujii et al.
2021/0038917 A1 2/2021 Karasawa et al.

FOREIGN PATENT DOCUMENTS

JP 2016-152992 A 8/2016
JP 6083761 B2 2/2017
JP 2017-209243 A 11/2017
JP 6668902 B2 3/2020
WO 2018/168766 A1 9/2018
WO 2018/225234 A1 12/2018

OTHER PUBLICATIONS

Extended European Search Report received in corresponding European Application No. 23756144.4 dated Dec. 11, 2025.

* cited by examiner

A
DATA SERVER
10
COMMUNICATION DEVICE
9
TREATMENT PLANNING SYSTEM
11
PATIENT POSITIONING DEVICE
20
IMAGE ACQUISITION PART
21
SIMULATED-X-RAY FLUOROSCOPIC IMAGE CREATION PART
22
ROI DRAWING PART
23
IMAGE COLLATION PART
24
IMAGE DISPLAY PART
25
CONTROL SECTION
26
TREATMENT-COUCH CONTROL SYSTEM
13
X-RAY FLUOROSCOPIC IMAGING DEVICE
12
1
2
3
4
5A
5B
6A
6B
7
8
B

RADIOTHERAPY DEVICE COMPRISING A POSITIONING DEVICE, AND POSITIONING METHOD

TECHNICAL FIELD

The present disclosure relates to a positioning device, a radiotherapy device, and a positioning method.

BACKGROUND ART

One known example of a cancer treatment method is radiotherapy, in which a patient is irradiated with radiation. The radiation used in radiotherapy is broadly classified into uncharged particle beam such as X-ray or gamma ray, and charged particle beam such as proton beam or carbon beam. Radiotherapy using the latter charged particle beam is generally called particle therapy.

In the case of an uncharged particle beam, the dose decreases at a constant rate from a shallow position to a deep position in the body. On the other hand, in the case of a charged particle beam, a dose distribution (black curve) having a peak of energy loss at a specific depth can be formed. Therefore, by matching the peak of the energy loss of the charged particle beam with the position of a tumor, it is possible to greatly reduce the dose of the charged particle beam with which normal tissue at a position deeper than the tumor is irradiated.

For this reason, in radiotherapy, it is important to accurately irradiate a target tumor with a desired dose of radiation to improve the therapeutic effect. In order to accurately irradiate the tumor with radiation, it is necessary to align the position of the patient in the same position as the planned position determined by a treatment plan created in advance. This alignment of the patient position is called patient positioning.

As a method for positioning a patient in radiotherapy, there is a method which uses X-ray fluoroscopic images (Digital Radiography: DR) obtained by imaging a patient lying on a treatment-couch from two different directions by two sets of X-ray tubes and a flat panel detector (FPD). In this method, an X-ray fluoroscopic image obtained by imaging a patient at the time of radiotherapy is compared with a simulated-X-ray fluoroscopic image created from a computed tomography (CT) image which is used when creating a treatment plan, and positioning of the patient is performed such that there is a match in the position of a positioning target structure such as a bone between the X-ray fluoroscopic image and the simulated-X-ray fluoroscopic image.

In general, an X-ray fluoroscopic image may include structures other than a structure which is to be positioned, such as soft tissue and tools for securing the patient, or the placement of a bone, which is a structure to be positioned, may change from the time of the treatment plan. In such a situation, the structure captured in the X-ray fluoroscopic image and the simulated-X-ray fluoroscopic image do not match one another across the entire image. In this case, the patient is positioned using a region of interest (ROI), which is set as a region, on the X-ray fluoroscopic image, where the structure to be positioned is present. Note that the setting of the region of interest is usually performed by a user who is a medical worker drawing the region of interest on an image.

Automatic alignment to position the patient is performed by using the translation amount and the rotation amount of the treatment-couch on which the patient is sleeping as parameters and using an optimization calculation to calculate optimum values of the parameters. Normally, the translation amount has three components along three axes (x, y, z) orthogonal to each other, and the rotation amount has three components (pitch, roll, and yaw) for which the three axes serve as rotation axes. Therefore, in the optimization calculation, the optimization process for each of the six components is repeatedly performed to calculate the optimum values of the parameters. Furthermore, the three axes defining the translation amount coincide with the axes of motion of the treatment-couch for placing the patient in a planned position, the x axis being oriented in a direction from right to left (a right-left (RL) direction) as viewed from the patient lying on the treatment-couch on their back, the y axis being oriented in a direction from the foot to the head (a superior-inferior (SI) direction), and the z axis being oriented in a direction from the back to the abdomen (an anterior-posterior (AP) direction).

However, in a case where the position of the patient at the start of positioning is far from the planned position, the change in the similarity between the images serving as the determination indexes is small in the optimization calculation, and it is not possible to use such a feature that the similarity increases toward the optimum position, and the optimum value of the parameter cannot be reached, or the calculation time may increase due to an increase in the number of repeated calculations in the optimization calculation.

In contrast, PTLs 1 and 2 disclose techniques for achieving an optimum value by using a smaller number of repetitive calculations. In these techniques, in the optimization calculation, by adding an optimization process in a one-dimensional direction with respect to a direction along the imaging axis for capturing the X-ray fluoroscopic image after the optimization process for each component is completed, the number of calculations for repeating the optimization process in the optimization calculation is reduced.

In addition, PTL 3 discloses a technique of reducing the number of X-ray fluoroscopic images by evaluating the optimization of the translation amount with respect to the direction along the imaging axis only in one direction orthogonal to the fluoroscopic imaging axis, thereby reducing the time taken to position the patient.

CITATION LIST

Patent Literatures

PTL 1: Japanese Patent No. 6668902
PTL 2: WO 2018/225234 A
PTL 3: JP 2013-99431 A

SUMMARY OF INVENTION

Technical Problem

However, in the techniques disclosed in PTLs 1 to 3, there is no change in performing optimization using the similarity of images. Therefore, in a case where the position of the patient at the start of positioning is far away from the planned position and the change in the similarity between images becomes small, or other such cases, it may not be possible to suppress an increase in calculation time due to an increase in the number of repeated calculations in the optimization calculation.

An object of the present disclosure is to provide a positioning device, a radiotherapy device, and a positioning method that enable a further reduction in calculation time.

Solution to Problem

A positioning device according to one aspect of the present disclosure is a positioning device that controls a position of a treatment-couch on which a subject is mounted, the positioning device including: an image acquisition part that acquires a plurality of fluoroscopic images obtained by imaging the subject by detecting, on a detection surface via the subject, light from a light source for each of a plurality of imaging axes; a creation part that creates, for each of the plurality of imaging axes, a simulated fluoroscopic image obtained by projecting a three-dimensional fluoroscopic image of the subject onto a detection surface with respect to the imaging axis; and a calculation processing part that obtains, for each of the plurality of imaging axes, a correction axis obtained by correcting the imaging axis based on a deviation amount between the fluoroscopic image and the simulated fluoroscopic image corresponding to the imaging axis, and calculates, as a treatment-couch motion amount by which the treatment-couch is to be moved, a motion amount from an intersection of the plurality of imaging axes to a midpoint of a common perpendicular of the correction axes.

Advantageous Effects of Invention

The present invention enables a further reduction in the calculation time.

DESCRIPTION OF EMBODIMENT

Figure 1:
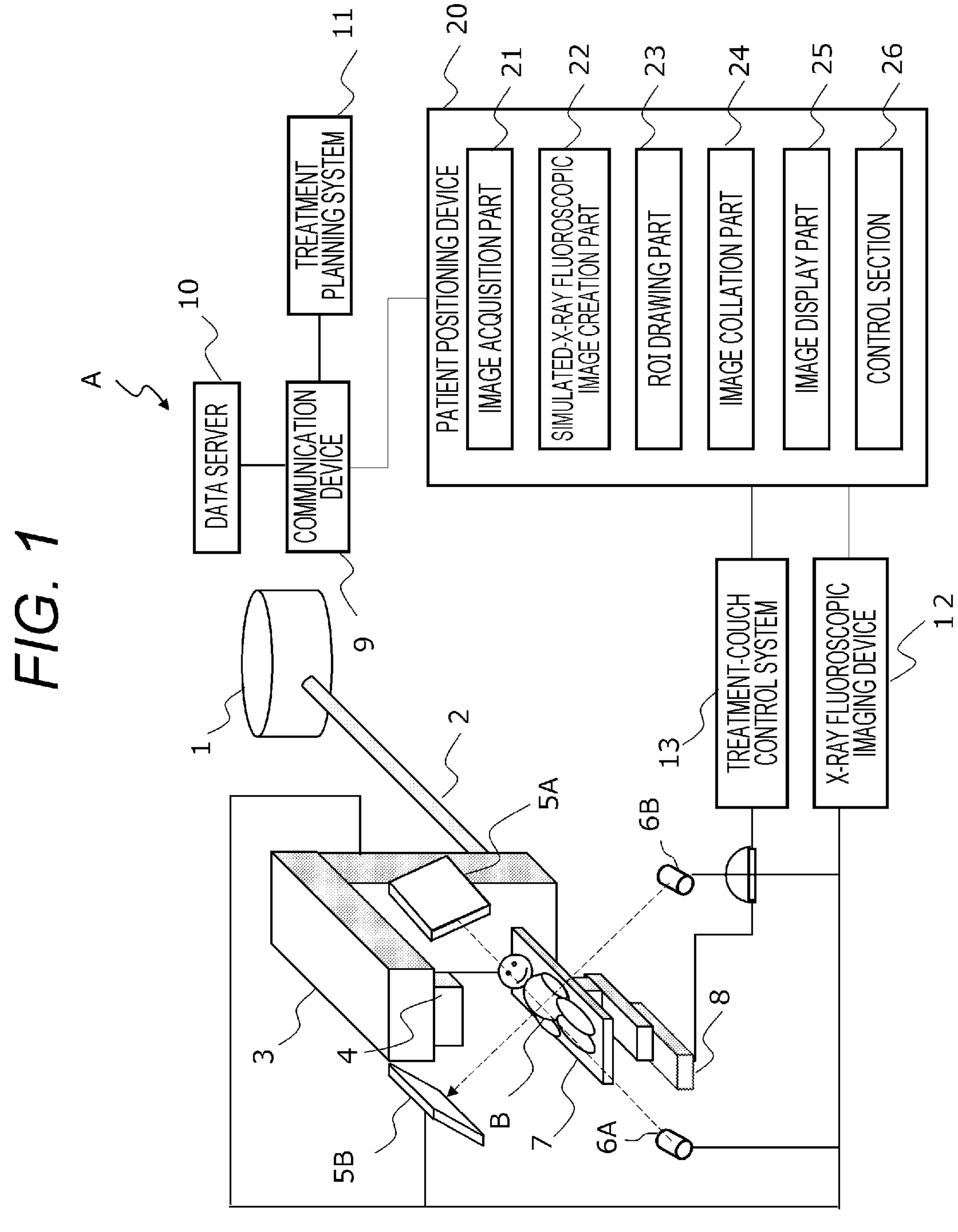
FIG. 1 is a diagram illustrating a general arrangement of a particle therapy system according to an embodiment of the present disclosure.

Hereinafter, an embodiment of the present disclosure will be described with reference to the drawings.

Note that the descriptions and drawings hereinbelow are examples to illustrate the present invention, and omissions and simplifications are made, as appropriate, to clarify the invention. The present invention can also be carried out in various other modes. Unless otherwise specified, each constituent element may be singular or plural. Note that, in all the drawings to illustrate the embodiment, parts having the same functions are assigned the same reference signs, and repetitive descriptions thereof will be omitted. In addition, the position, size, shape, range, and the like of each constituent element illustrated in the drawings may not represent the actual position, size, shape, range, and the like, in order to facilitate understanding of the invention. Therefore, the present invention is not limited to or by the position, size, shape, range, and the like disclosed in the drawings. Further, in a case where there is a plurality of constituent elements having the same or similar functions, same may be described with different subscripts added to the same reference signs. However, in a case where it is not necessary to distinguish between a plurality of constituent elements, descriptions may sometimes be provided with the subscripts omitted.

FIG. 1 is a diagram illustrating a general arrangement of a particle therapy system according to an embodiment of the present disclosure. A particle therapy system A illustrated in FIG. 1 is a radiotherapy device having a group of devices for irradiating a patient B, who is a subject, with a particle beam as a target. The particle therapy system A includes an accelerator 1, a beam transport system 2, a gantry 3, an irradiation nozzle 4, FPDs 5A and 5B, X-ray tubes 6A and 6B, a treatment-couch 7, a robot arm 8, a communication device 9, a data server 10, a treatment planning system 11, an X-ray fluoroscopic imaging device 12, a treatment-couch control system 13, and a patient positioning device 20.

The accelerator 1 is a particle beam generator that generates a particle beam for irradiating patient B, and accelerates and outputs the particle beam until the particle beam has energy suitable for treatment of patient B. The beam transport system 2 transports the particle beam output from the accelerator 1 to the gantry 3. The type of the particle beam is not particularly limited, and is, for example, a proton beam or a carbon beam, or the like.

The gantry 3 and the irradiation nozzle 4 are irradiation devices that irradiate patient B with the particle beam transported from the accelerator 1. The gantry 3 adjusts an irradiation angle at which patient B is irradiated with the particle beam transported from the accelerator 1. Specifically, the gantry 3 has a rotation mechanism capable of rotating 360° around patient B, and adjusts the irradiation angle by rotating. The irradiation nozzle 4 is provided to the gantry 3 and irradiates patient B with the particle beam transported to the gantry 3. A mechanism for adjusting the shape of the particle beam to match the shape of the target volume of the patient may be incorporated in the irradiation nozzle 4.

The FPDs 5A and 5B and the X-ray tubes 6A and 6B constitute an imaging system that performs fluoroscopic imaging of patient B. The FPDs 5A and 5B are plane detectors that capture images of patient B by detecting X-rays, which are imaging light, on a detection surface. The X-ray tubes 6A and 6B are light sources that output X-rays. The FPD 5A and the X-ray tube 6A are arranged to face each other such that the X-rays output from the X-ray tube 6A are detected by the FPD 5A through patient B, and the FPD 5B and the X-ray tube 6B are arranged to face each other such that the X-rays output from the X-ray tube 6B are detected by the FPD 5B through patient B. An axis connecting the center of the FPD 5A to the X-ray tube 6A and an axis connecting the center of the FPD 5B to the X-ray tube 6B are two imaging axes for imaging patient B. The two imaging axes are preferably orthogonal to each other, but need not be orthogonal to each other. The particle therapy system A may include three or more FPDs and three or more X-ray tubes. In this case, the number of imaging axes is also three or more.

The treatment-couch 7 is a table on which patient B is mounted when patient B is irradiated with the particle beam. The robot arm 8 is a device that moves the treatment-couch 7. Specifically, the robot arm 8 performs, with respect to the treatment-couch 7, translational motion in a plurality of translational directions along each of a plurality of axes of motion and rotational motion in a plurality of rotational directions about a plurality of rotation axes. In the present embodiment, a rotation axis is the same as an axis of motion, and there are three axes of motion (rotation axes). In addition, each axis of motion is directed in a direction from right to left (RL direction) as viewed from patient B lying on the treatment-couch 7 on their back, a direction from the foot to the head (SI direction) of patient B, and a direction from the back to the abdomen (AP direction).

The communication device 9 communicably connects the data server 10, the treatment planning system 11, and the patient positioning device 20 to each other.

The data server 10 is a storage device that stores various types of information regarding the particle therapy of patient B. The data server 10 stores, for example, a three-dimensional fluoroscopic image of patient B and treatment plan information indicating a treatment plan for patient B. The three-dimensional fluoroscopic image includes information indicating the shape and electron density of the patient in voxel units. The three-dimensional fluoroscopic image is, for example, a computed tomography (CT) captured image, and is generated in advance (before creating treatment plan information on patient B). The treatment plan information is generated based on a three-dimensional fluoroscopic image. In addition, the treatment plan information includes planned placement information indicating a planned placement, which is a placement for patient B at the time of treatment. The placement of patient B indicates the position and angle (posture) of patient B and is determined by the position and angle of the treatment-couch 7.

The treatment planning system 11 creates a treatment plan for patient B based on the three-dimensional fluoroscopic image stored in the data server 10, and stores, in the data server 10, treatment plan information indicating the treatment plan.

The X-ray fluoroscopic imaging device 12 controls each of the FPD 5A and the X-ray tube 6A, and the FPD 5B and the X-ray tube 6B, acquires a plurality of X-ray fluoroscopic images obtained by imaging patient B from different angles as fluoroscopic images, and transmits the acquired X-ray fluoroscopic images to the patient positioning device 20. In the present embodiment, there are two X-ray fluoroscopic images.

The treatment-couch control system 13 adjusts the placement of patient B by controlling the robot arm 8 to adjust the placement of the treatment-couch 7.

The patient positioning device 20 executes positioning processing of patient B based on the three-dimensional fluoroscopic image and the treatment plan information which are stored in the data server 10, and the X-ray fluoroscopic image acquired by the X-ray fluoroscopic imaging device 12.

The positioning processing of patient B is processing, before starting the particle therapy of patient B, in which patient B, who is lying on the treatment-couch 7, is placed in the same manner as the planned placement indicated by the treatment plan information. The patient positioning device 20 controls the robot arm 8 via the treatment-couch control system 13 to adjust the position and angle of the treatment-couch 7, thereby placing patient B in the same manner as the planned placement.

When the positioning processing is complete, the particle therapy on patient B is actually performed. Specifically, the particle beam accelerated to energy suitable for treatment by the accelerator 1 is transported to the gantry 3 via the beam transport system 2. The particle beam is deflected in an appropriate direction by the gantry 3 and passes through the irradiation nozzle 4 to irradiate the target volume of patient B.

Hereinafter, the patient positioning device 20 will be described in more detail.

As illustrated in FIG. 1, the patient positioning device 20 includes an image acquisition part 21, a simulated-X-ray fluoroscopic image creation part 22, an ROI drawing part 23, an image collation part 24, an image display part 25, and a control section 26.

The image acquisition part 21 acquires a three-dimensional fluoroscopic image from the data server 10 via the communication device 9, and acquires the X-ray fluoroscopic image from the X-ray fluoroscopic imaging device 12.

The simulated-X-ray fluoroscopic image creation part 22 is a creation part that creates a plurality of simulated-X-ray fluoroscopic images which are a plurality of simulated fluoroscopic images obtained by projecting a three-dimensional fluoroscopic image acquired by the image acquisition part 21 onto each of a plurality of planes corresponding to each imaging axis for capturing the X-ray fluoroscopic image. The simulated-X-ray fluoroscopic image creation part 22 creates the simulated-X-ray fluoroscopic images by placing the three-dimensional image of patient B on the same virtual space as the imaging system that generated the X-ray fluoroscopic image and performing projection processing. The surface corresponding to the imaging axis is, for example, a detection surface of the FPD corresponding to the imaging axis, that is, a surface substantially orthogonal to the imaging axis.

The ROI drawing part 23 specifies an ROI which is a region of interest, on the simulated-X-ray fluoroscopic image, which is for used positioning the patient. Specifically, the ROI drawing part 23 specifies the ROI by displaying the simulated-X-ray fluoroscopic image to enable the user to draw the ROI on the simulated-X-ray fluoroscopic image. The ROI is drawn to include, for example, a structure to be positioned such as a bone.

The image collation part 24 is a calculation processing part that calculates a treatment-couch motion amount by which the treatment-couch 7 is to be moved, based on the X-ray fluoroscopic image and the simulated-X-ray fluoroscopic image. In a case where the ROI is designated by the ROI drawing part 23, the image collation part 24 may calculate the treatment-couch motion amount based on the X-ray fluoroscopic image in the ROI and the simulated-X-ray fluoroscopic image. In the present embodiment, the treatment-couch motion amount includes the motion amount in each of the plurality of translation directions.

The image display part 25 is a display part that displays various types of information and images. For example, the image display part 25 displays X-ray fluoroscopic images, simulated-X-ray fluoroscopic images, and ROI images indicating an ROI region, and the like.

The control section 26 controls the treatment-couch control system 13 based on the treatment-couch motion amount calculated by the image collation part 24 to move the treatment-couch 7, thereby adjusting the placement of patient B.

The patient positioning device 20 having the above functions can be implemented by means of an information processing device capable of performing various types of information processing, such as a computer device. The information processing device includes, for example, an arithmetic element, a storage medium, and a communication interface, and, if necessary, further includes an input part such as a mouse and a keyboard, and a display part such as a display.

The arithmetic element is, for example, a processor such as a central processing unit (CPU) and a field-programmable gate array (FPGA). Examples of the storage medium include a magnetic storage medium such as a hard disk drive (HDD), and a semiconductor storage medium such as a randomaccess memory (RAM), a read-only memory (ROM), and a solid state drive (SSD). In addition, a combination of an optical disk such as a digital versatile disk (DVD) and an optical disk drive may be used as the storage medium. Another high-value storage medium such as a magnetic tape medium may also be used as the storage medium.

A program such as firmware is stored on the storage medium. When the operation of the patient positioning device 20 is started (for example, when the power is turned on), the arithmetic element reads the program from the storage medium and executes the program, thus realizing parts 21 to 27 of the patient positioning device 20, and executing an entire series of control processes. In addition to the program, the storage medium stores data and the like necessary for each instance of processing of the patient positioning device 20.

Note that the patient positioning device 20 according to the present embodiment may be configured by so-called cloud computing in which a plurality of information processing devices are capable of communicating via a communication network.

Hereinafter, the patient positioning processing by the patient positioning device 20 will be described in more detail with reference to FIGS. 2 to 5.

Figure 2:
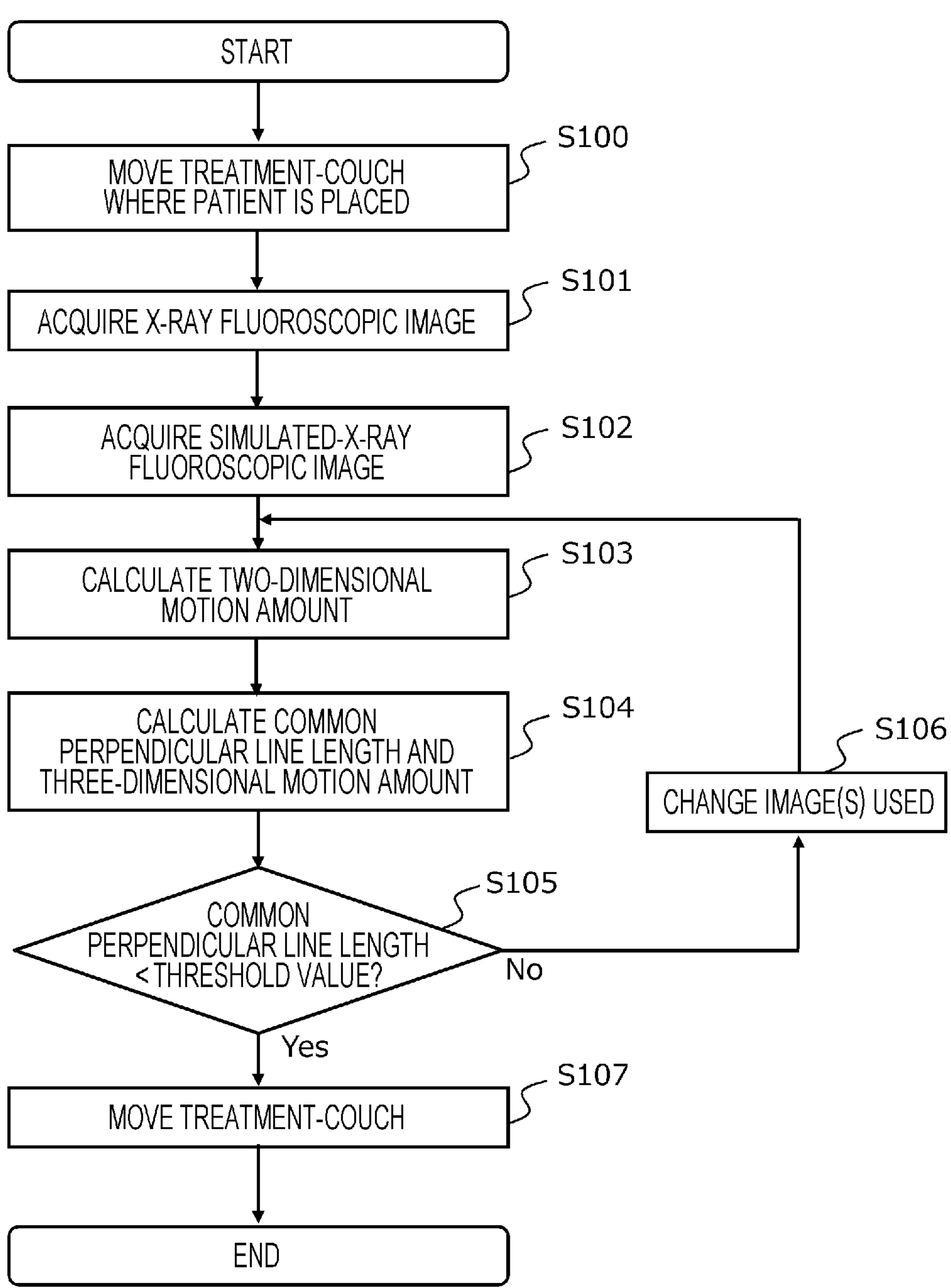
FIG. 2 is a flowchart to illustrate an example of patient positioning processing.

FIG. 2 is a flowchart to illustrate an example of patient positioning processing.

Note that it is assumed that patient B is arranged in a setup position of the treatment-couch 7. The setup position is a position for placing patient B in the same manner as the planned placement. For example, the position of the surface of the body of patient B on the treatment-couch 7 is measured using an infrared laser installed in the treatment room, and patient B is placed in the setup position of the treatment-couch 7 based on this position.

In the patient positioning processing, first, the control section 26 acquires treatment plan information from the data server 10, and controls the robot arm 8 via the treatment-couch 1 system 13 based on the planned placement information included in the treatment plan information to move the treatment-couch 7 on which patient B is lying so that the placement of patient B is the planned placement indicated by the planned placement information (step S100). At this time, the positioning target structure of patient B lying on the treatment-couch 7 is included in the X-ray irradiation region formed by the FPDs 5A and 5B and the X-ray tubes 6A and 6B.

Thereafter, the image acquisition part 21 acquires a plurality of X-ray fluoroscopic images obtained by imaging patient B from a plurality of different directions via the X-ray fluoroscopic imaging device 12 (step S101). In the present embodiment, the image acquisition part 21 acquires two X-ray fluoroscopic images captured from two directions along two imaging axes.

The simulated-X-ray fluoroscopic image creation part 22 acquires the three-dimensional fluoroscopic image from the data server 10, and creates two simulated-X-ray fluoroscopic images corresponding to the two imaging axes from the three-dimensional fluoroscopic image (step S102).

The image collation part 24 calculates, for each imaging axis, an amount of deviation in the two-dimensional direction between an X-ray fluoroscopic image and a simulated-X-ray fluoroscopic image corresponding to the imaging axis, as the two-dimensional motion amount, on the detection surface, of the FPD corresponding to the imaging axis (step S103).

As a calculation method for calculating an image deviation amount, a method is known in which the simulated-X-ray fluoroscopic image is scanned in the horizontal direction and the vertical direction with respect to the X-ray fluoroscopic image to search for a position in which the similarity between the images is the highest. However, using this method, sequential calculation of the similarity is necessary, and the calculation amount increases. Therefore, in the present embodiment, a calculation method using a phase-only correlation method (POC) method, which is known as a method enabling image collation at high-speed, will be described.

The POC method is a method for performing image matching (alignment) using only a phase component obtained from two-dimensional discrete Fourier transform on an image, and has a feature of being resistant to disturbance such as a change in image luminance. In addition, the POC method differs from a method for performing matching based on feature points of an image such as edges or corners, and enables alignment to be performed accurately even for images in which no clear features are present.

In the present embodiment, the image collation part 24 calculates a two-dimensional motion amount, which is the deviation amount between an X-ray fluoroscopic image and a simulated-X-ray fluoroscopic image, by using a POC function (phase-only correlation function), which is used as a matching evaluation index according to the POC method.

Here, two images to be subjected to a calculation method using the POC method are set as images $f(n_1, n_2)$ and $g(n_1, n_2)$. Images $f(n_1, n_2)$ and $g(n_1, n_2)$ are both images having $N_1 \times N_2$ pixels. $n_1$ and $n_2$ are discrete spatial indexes indicating pixels, and $n_1=-M_1, \ldots, M_1$, $n_2=-M_2, \ldots, M_2$. Note that $n_1$ and $n_2$ are integers, $M_1$ and $M_2$ are positive integers, and $N_1=2M_1+1$ and $N1=2M_1+1$ are satisfied.

The two-dimensional discrete Fourier transform (DFT) of the images $f(n_1, n_2)$ and $g(n_1, n_2)$ is expressed by the following Formulas (1) and (2).

[Equation 1]

$$F(k_1, k_2) = \sum_{n_1, n_2} f(n_1, n_2) W_{N_1}^{k_1 n_1} W_{N_2}^{k_2 n_2} = A_F(k_1, k_2) e^{j\theta_F(k_1, k_2)} \tag{1}$$

$$G(k_1, k_2) = \sum_{n_1, n_2} g(n_1, n_2) W_{N_1}^{k_1 n_1} W_{N_2}^{k_2 n_2} = A_G(k_1, k_2) e^{j\theta_G(k_1, k_2)} \tag{2}$$

Here, $k_1(=-M_1, \ldots, M_1)$ and $k_2(=-M_2, \ldots, M_2)$ are discrete frequency indexes (integers), and $W_{N1}=\exp(-j\cdot 2\pi/N1)$ and $W_{N1}=\exp(-j\cdot 2\pi/N_2)$ are rotation factors. $A_F(k_1, k_2)$ and $A_G(k_1, k_2)$ are amplitude spectra, and $\theta_F(k_1, k_2)$ and $\theta_G(k_1, k_2)$ are phase spectra. In addition, the sum $\Sigma_{n1,n2}$ indicates a sum $\Sigma_{n1=-M1}^{M1}\Sigma_{n2=-M2}^{M2}$ across the entire discrete space index.

The normalized mutual power spectra of the images $f(n_1, n_2)$ and $g(n_1, n_2)$ are expressed by the following Formula (3) using the functions $F(k_1, k_2)$ and $G(k_1, k_2)$ after the Fourier transform.

[Equation 2]

$$R(k_1, k_2) = \frac{F(k_1, k_2)\overline{G(k_1, k_2)}}{\left|F(k_1, k_2)\overline{G(k_1, k_2)}\right|} = e^{j\{\theta_F(k_1, k_2) - \theta_G(k_1, k_2)\}} \tag{3}$$

where:

$\overline{G(k_1,k_2)}$ [Equation 3]

denotes the complex conjugate of G $(k_1, k_2)$. In addition, $\{\theta_F(k_1, k_2)-\theta_G(k_1, k_2)\}$ is a phase difference spectrum of the images $f(n_1, n_2)$ and $g(n_1, n_2)$.

The POC function $r(n_1, n_2)$ is defined as a two-dimensional inverse discrete Fourier transform (IDFT) of the normalized mutual power spectrum by the following equation (4).

[Equation 4]

$$r(n_1, n_2) = \frac{1}{N_1, N_2} \sum_{k_1, k_2} R(k_1, k_2) W_{N_1}^{-k_1 n_1} W_{N_2}^{-k_2 n_2} \tag{4}$$

Here, the sum $\Sigma_{k1,\ k2}$ indicates a sum $\Sigma_{k1=-M1}^{M1} \Sigma_{k2=-M2}^{M2}$ across the entire discrete frequency index.

The POC function has a sharp peak called a correlation peak in a case where the images of interest $f(n_1, n_2)$ and $g(n_1, n_2)$ are similar to each other. The height of the correlation peak represents the linearity of the phase difference spectrum of the images $f(n_1, n_2)$ and $g(n_1, n_2)$ with respect to the frequency, and when the phase difference spectrum is linear with respect to the frequency, the height of the correlation peak is 1. The height of the correlation peak is useful as a measure representing image similarity, and is used in image matching and the like. Furthermore, the coordinates of the correlation peak represent a relative deviation amount of the image. For example, the amount of coordinate deviation of the correlation peak with respect to the image origin (n1=0, n2=0) can be used as the deviation amount of the images $f(n_1, n_2)$ and $g(n_1, n_2)$.

Note that, using the two-dimensional DFT, because cyclic convolution is assumed at the edge of the target image, discontinuity that should not originally exist appears at the edge of the image. In the present embodiment, in order to reduce such discontinuity, the image collation part 24 calculates the two-dimensional motion amount by using, as the images $f(n_1, n_2)$ and $g(n_1, n_2)$, images obtained by multiplying the X-ray fluoroscopic image and the simulated-X-ray fluoroscopic image by a window function. The window function is, for example, a two-dimensional Hanning window $(w(n_1, n_2)$ expressed by Formula (5).

[Equation 5]

$$w(n_1, n_2) = \frac{1 + \cos\left(\frac{\pi n_1}{M_1}\right)}{2} \cdot \frac{1 + \cos\left(\frac{\pi n_2}{M_2}\right)}{2} \tag{5}$$

Using the POC method as described above, the image collation part 24 calculates, for each imaging axis, the amount of deviation in the two-dimensional direction between the position and the origin of the correlation peak of the phase-only correlation function calculated from the X-ray fluoroscopic image and the simulated-X-ray fluoroscopic image, as the two-dimensional motion amount.

The description now returns to FIG. 2. The image collation part 24 executes three-dimensional motion amount calculation processing to calculate, as a treatment-couch motion amount by which the treatment-couch 7 is to be moved, a three-dimensional motion amount, based on the two-dimensional motion amount of each imaging axis (step S104).

In the three-dimensional motion amount calculation processing, the image collation part 24 first obtains, for each imaging axis, a correction axis obtained by correcting the imaging axis based on a two-dimensional motion amount, which is a deviation amount between the X-ray fluoroscopic image and the simulated-X-ray fluoroscopic image corresponding to the imaging axis. The image collation part 24 then calculates the motion amount from the intersection of the respective imaging axes to the midpoint of the common perpendicular of the respective correction axes, as the three-dimensional motion amount constituting the treatment-couch motion amount.

Figure 3:
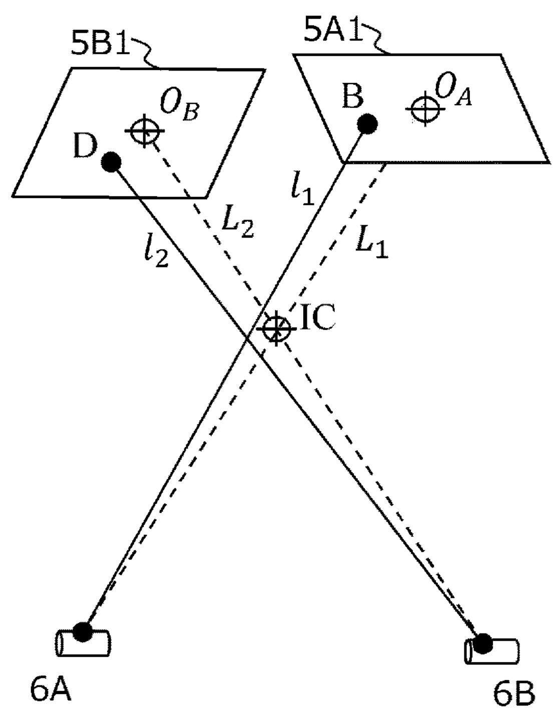
FIG. 3 is a diagram to illustrate processing to obtain a correction axis from a two-dimensional motion amount.
Figure 4:
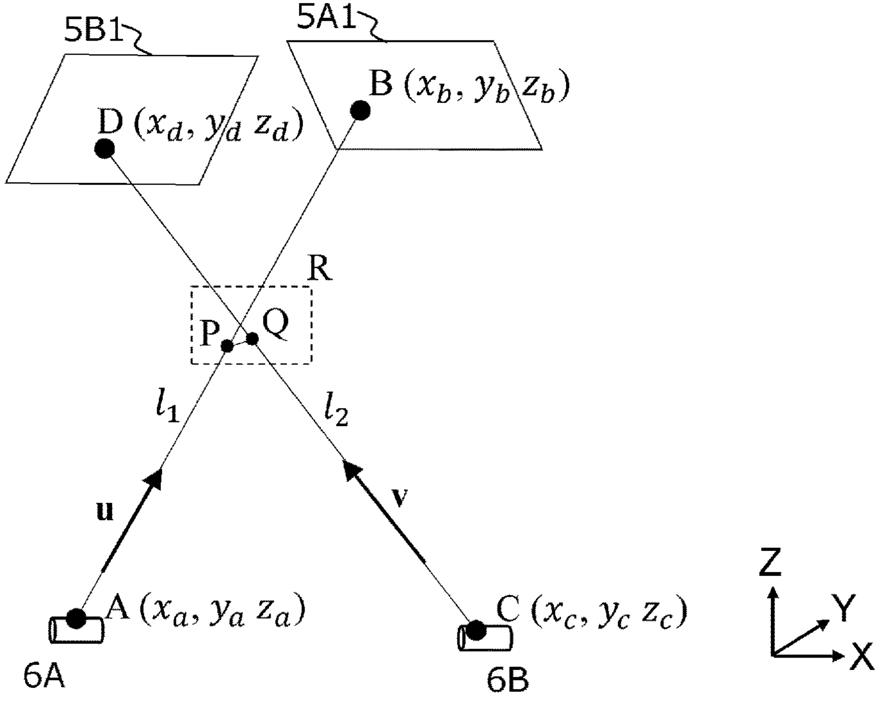
FIG. 4 is a diagram to illustrate processing to obtain a three-dimensional motion amount from a correction axis.
Figure 5:
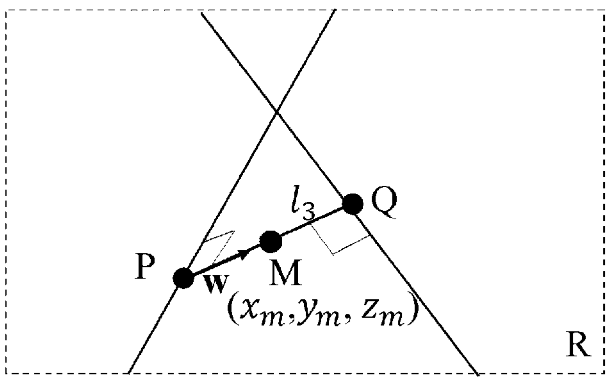
FIG. 5 is an enlarged view of a common perpendicular illustrated in FIG. 4.

FIGS. 3 to 5 are diagrams to illustrate three-dimensional motion amount calculation processing in more detail. Specifically, FIG. 3 is a diagram to illustrate processing to obtain a correction axis from a two-dimensional motion amount; FIG. 4 is a diagram to illustrate processing to obtain a three-dimensional motion amount from a correction axis; and FIG. 5 is an enlarged view of the common perpendicular illustrated in FIG. 4. Note that it is assumed that the distortion of the X-ray fluoroscopic image is removed in advance through distortion correction according to the placement angle of the FPDs 5A and 5B. The distortion correction may be performed by, for example, an imaging device that captures X-ray fluoroscopic images, or may be performed using the patient positioning device 20. In addition, even if the distortion correction is not performed, the following three-dimensional motion amount calculation processing can be performed.

As illustrated in FIG. 3, the center point of the detection surface 5A1 of the FPD 5A is defined as OA, and the center point of the detection surface 5B1 of the FPD 5B is defined as $O_B$. The imaging axes are a line $L_1$ connecting the center point $O_A$ of the detection surface 5A1 to the X-ray tube 6A, and a line L2 connecting the center point OB of the detection surface 5B1 to the X-ray tube 6B.

The image collation part 24 sets an intersection of the imaging axes $L_1$ and L2 as a reference position IC (origin of the coordinate system), and sets, as correction axes, a line $l_1$ connecting the position where the reference position IC is moved along the detection surface 5A1 of the FPD 5A by the two-dimensional motion amount corresponding to the imaging axis $L_1$ to the X-ray tube 6A, and a line $l_2$ connecting the position where the reference position IC is moved along the detection surface 5B1 of the FPD 5B by the two-dimensional motion amount corresponding to the imaging axis L2 to the X-ray tube 6B.

As illustrated in FIG. 4, the position of the X-ray tube 6A is A $(X_a, Y_a, Z_a)$, the position of the matched center point on the detection surface 5A1 of the FPD 5A is B $(x_b, y_b, z_b)$, the position of the X-ray tube 6B is C $(x_c, y_c, z_c)$, and the position of the matched center point on the detection surface 5B1 of the FPD 5B is D $(x_d, y_d, z_d)$. The coordinates of each of the positions A to D are three-dimensional coordinates in a coordinate system (X, Y, Z) set in advance in the treatment room in which the gantry 3 and the treatment-couch 7 are arranged, and the reference position IC is set as the origin of the coordinate system. The matched center point is an intersection point between the correction axes $l_1$ and $\mathbf{1}_2$ and the detection surfaces 5A1 and 5B1.

The lines $l_1$ and $l_2$, which are the correction axes, ideally intersect with each other, but in practice may not intersect with each other due to a minute error in the position of the matched center point, which depends on the image resolution, and a minute deviation in machine placement between the FPDs 5A and 5B and the X-ray tubes 6A and 6B, and the like.

In a case where the line $l_1$ and the line $l_2$ do not intersect with each other, the image collation part 24 sets the points at which the distance between the line $l_1$ and the line $l_2$ is the smallest on the lines $l_1$ and $l_2$ as points P and Q, and calculates the position of the midpoint of a line segment $l_3$ connecting point P and point Q using three-dimensional coordinates. Line $l_3$ is a common perpendicular that is perpendicular to both lines $l_1$ and $l_2$ that are twisted relative to each other. Hereinafter, the length of the line $l_3$ is referred to as the common perpendicular length. Points P and Q are the feet of the common perpendicular $l_3$.

Point P of the line $l_1$ and point Q of the line $l_2$ can be expressed as vectors using the parameter s and t as follows.

$$p = a + su$$

$$q = c + tv$$

Here, p is a position vector $(x_p, y_p, z_p)$ of point P, q is a position vector $(x_q, y_q, z_q)$ of point Q, a is a position vector $(x_a, y_a, z_a)$ of point A, c is a position vector $(x_c, y_c, z_c)$ of point C, u is a direction vector of the line $l_1$, and v is a direction vector of the line $l_2$.

Because the line segment PQ is orthogonal to each of the direction vectors u and v, the inner product of the direction vector w of the line segment PQ and the direction vectors u and v is zero. That is, $w \cdot u=0$ and $w \cdot v=0$. Note that the operator "·" indicates an inner product.

The values of the parameter variables s and t can be obtained by solving the two equations of the inner product as simultaneous linear equations. As a result, the coordinates of points P and Q and the common perpendicular length L, which is the length of the line segment PQ, are given as $L=|q-p|=(|p|+|q|-2p \cdot q)^{1/2}=\{(x_q-x_p)^2+(y_q-y_p)^2+(z_q-z_p)^2\}^{1/2}$.

Furthermore, coordinates $(x_m, y_m, z_m)M(x_m, y_m, z_m)=((x_q+x_p)/2, (y_q+y_p)/2, (z_q+z_p)/2)$ of the midpoint M of the line segment PQ are obtained. As a result, the three-dimensional motion amount is the motion amount from the intersection of the imaging axes to the midpoint M of line segment PQ, and in the present embodiment, because the intersection of the imaging axes is set as the origin, the value of the coordinates of the midpoint M of line segment PQ can be calculated as the three-dimensional motion amount, which is the treatment-couch motion amount.

The image collation part 24 calculates the three-dimensional motion amount and the common perpendicular length according to the above method. In a case where the lines 11 and 12, which are correction axes, intersect each other, the image collation part 24 calculates the three-dimensional motion amount by regarding the intersection of lines $l_1$ and $l_2$ as the midpoint M of line segment PQ.

The description now returns to FIG. 3. Upon calculating the three-dimensional motion amount and the common perpendicular length according to the above method in step 104, the image collation part 24 determines whether the common perpendicular length is less than a threshold value (for example, 1 mm) (step S105). Note that the common perpendicular length is ideally zero, that is, lines $l_1$ and $l_2$ intersect each other. The longer the common perpendicular length is, the less consistency is obtained between the two-dimensional motion amount and the three-dimensional motion amount of the simulated-X-ray fluoroscopic image and the X-ray fluoroscopic image. Further, the image collation part 24 may determine whether the correlation peak of the POC function is less than the threshold value instead of the common perpendicular length.

In a case where the common perpendicular length is equal to or greater than the threshold value (step S105: No), the image collation part 24 changes at least one of the X-ray fluoroscopic image and the simulated-X-ray fluoroscopic image (step S106), and returns to the processing of step S102.

Image changes are made, for example, by executing predetermined image processing on the images to be changed, which are at least one of the X-ray fluoroscopic image and the simulated-X-ray fluoroscopic image. The predetermined image processing is, for example, filter processing to highlight the edge of the image(s) to be changed, processing to extract a specific partial image from the image(s) to be changed, and the like. A partial image is, for example, an image indicating the ROI, and such processing may be executed by the ROI drawing part 23. In addition, when the processing of steps S103 to S104 is executed first, an image indicating the ROI extracted from the X-ray fluoroscopic image and the simulated-X-ray fluoroscopic image may be used. In this case, image changes may be executed by returning the partial image indicating the ROI to the original X-ray fluoroscopic image and the simulated-X-ray fluoroscopic image. The image changes may be realized by acquiring another X-ray fluoroscopic image from the X-ray fluoroscopic imaging device 12 or by creating another simulated-X-ray fluoroscopic image from another three-dimensional fluoroscopic image.

On the other hand, in a case where the common perpendicular length is less than the threshold value (step S105: Yes), the control section 26 moves the treatment-couch 7 via the treatment-couch control system 13 based on the three-dimensional motion amount calculated by the image collation part 24 (step S107), and ends the patient positioning processing. It is thus possible to move the patient from the current placement to the placement at the time of treatment planning, whereupon the actual particle beam irradiation is performed.

The patient positioning processing described above is merely an example, and the present invention is not limited thereto. For example, after calculating the treatment-couch motion amount by means of the above processing, the image collation part 24 may perform fine adjustment processing to calculate the translation amount and the rotation amount of the treatment-couch 7 by means of an optimization calculation based on the similarity between each corrected simulated fluoroscopic image obtained by correcting the simulated-x-ray fluoroscopic image based on the treatment-couch motion amount, and each fluoroscopic image. In this case, the control section 26 moves the treatment-couch 7 via the treatment-couch control system 13 based on the three-dimensional motion amount calculated by the image collation part 24 and the translation amount and the rotation amount calculated by the fine adjustment processing. For example, the control section 26 moves the treatment-couch 7 by the three-dimensional motion amount, and then translates and rotates the treatment-couch 7 by the translation amount and the rotation amount calculated by the fine adjustment processing. Note that the translation amount is calculated for each of the plurality of axes of motion of the treatment-couch 7, and the rotation amount is calculated for each of the plurality of axes of rotation of the treatment-couch 7.

In the fine adjustment processing, the image collation part 24 may perform the processing described in PTLs 1 to 3, for example. In addition, the image collation part 24 may perform processing to calculate, based on the similarity, the motion amount of the treatment-couch 7 such that each fluoroscopic image and each simulated fluoroscopic image maximally coincide with each other, for each of a plurality of translation directions along each of a plurality of optimization axes including a plurality of imaging axes and a plurality of rotation directions around a plurality of rotation axes.

In the present embodiment, a particle therapy system is illustrated as an example of the radiotherapy device, but the radiotherapy device is not limited to a particle therapy system, and may be a radiotherapy system using a non-particle beam such as X-rays. In this case, the accelerator 1 includes, for example, an electron beam accelerator that outputs X-rays.

As described above, according to the present embodiment, the image acquisition part 21 acquires a plurality of X-ray fluoroscopic images obtained by imaging the subject. For each imaging axis of the X-ray fluoroscopic image, the simulated-X-ray fluoroscopic image creation part 22 creates a simulated fluoroscopic image obtained by projecting a three-dimensional fluoroscopic image of the subject onto the detection surface with respect to the imaging axis. For each of the plurality of imaging axes, the image collation part 24 obtains a correction axis obtained by correcting the imaging axis based on a two-dimensional motion amount, which is a deviation amount between the X-ray fluoroscopic image and the simulated-X-ray fluoroscopic image corresponding to the imaging axis, and calculates, as a treatment-couch motion amount by which the treatment-couch is to be moved, a motion amount from an intersection of the imaging axes to a midpoint of a common perpendicular of the correction axes. Therefore, because the patient can be positioned without performing a repetitive calculation in the optimization calculation, the calculation time can be further reduced.

Further, in the present embodiment, the image collation part 24 obtains, as the correction axis, an axis connecting the position where the intersection of the imaging axes is moved by the two-dimensional motion amount, to the X-ray tube, for each of the plurality of imaging axes. In this case, it is possible to calculate a suitable correction axis according to the deviation between the X-ray fluoroscopic image and the simulated-X-ray fluoroscopic image, and thus more accurate positioning becomes possible.

In the present embodiment, the image collation part 24 calculates the two-dimensional motion amount based on the position of the peak of the phase-only correlation function calculated from the X-ray fluoroscopic image and the simulated-X-ray fluoroscopic image. In this case, because the two-dimensional motion amount can be calculated without performing sequential calculation such as optimization calculation, the calculation time can be further reduced.

In the present embodiment, the image collation part 24 calculates the phase-only correlation function from the ROI set on the X-ray fluoroscopic image and the simulated-X-ray fluoroscopic image. Therefore, the two-dimensional motion amount can be calculated more appropriately.

Further, in the present embodiment, in a case where the length of the common perpendicular of the correction axes is equal to or greater than the threshold value, the image collation part 24 changes at least one of the X-ray fluoroscopic image and the simulated-X-ray fluoroscopic image to redetermine the correction axis. In this case, it is possible to obtain a correction axis with which the two-dimensional motion amount and the three-dimensional motion amount of the simulated-X-ray fluoroscopic image and the X-ray fluoroscopic image are further aligned, and thus more accurate positioning becomes possible.

Furthermore, in the present embodiment, the image changes are executed by performing predetermined image processing. Therefore, it is not necessary to re-image the X-ray fluoroscopic image or re-create the simulated-X-ray fluoroscopic image from a three-dimensional fluoroscopic image, thereby enabling a further reduction in the calculation time.

In the present embodiment, the image collation part 24 further calculates the motion amounts in the translation direction and the rotation direction of the treatment-couch 7 based on the similarity between each corrected simulated fluoroscopic image obtained by correcting each simulated-X-ray fluoroscopic image based on the treatment-couch motion amount, and each fluoroscopic image. In this case, more accurate positioning is possible. Note that, even in this case, because each simulated fluoroscopic image is corrected based on the treatment-couch motion amount, it is possible to prevent the position of the patient at the start of fine adjustment from being greatly separated from the planned position, and hence it is possible to suppress an increase in the number of repeated calculations in the optimization calculation. Therefore, the calculation time can be further reduced.

The above-described embodiment of the present disclosure is an example to illustrate the present disclosure and is not intended to limit the scope of the present disclosure only to this embodiment. A person skilled in the art is able to carry out the present disclosure in various other aspects without departing from the scope of the present disclosure.

REFERENCE SIGNS LIST

A particle therapy system
B patient
1 accelerator
2 beam transport system
3 gantry
4 irradiation nozzle
5A FPD
5B FPD
6A X-ray tube
6B X-ray tube
7 treatment-couch
8 robot arm
9 communication device patient
10 data server
11 treatment planning system
12 X-ray fluoroscopic imaging device
13 treatment-couch control system
20 patient positioning device
21 simulated-X-ray fluoroscopic image creation part
23 ROI drawing part
24 image collation part
25 image display part
26 control section

The invention claimed is:

1. A positioning device that controls a position of a treatment-couch on which a subject is mounted, the positioning device comprising:

an image acquisition part that acquires a plurality of fluoroscopic images obtained by imaging the subject by detecting, on a detection surface via the subject, light from a light source for each of a plurality of imaging axes;

a creation part that creates, for each of the plurality of imaging axes, a simulated fluoroscopic image obtained by projecting a three-dimensional fluoroscopic image of the subject onto the detection surface with respect to each imaging axis of the plurality of imaging axes; and a calculation processing part that obtains, for each of the plurality of imaging axes, a correction axis obtained by correcting each imaging axis of the plurality of imaging axes based on a deviation amount between a fluoroscopic image of the plurality of fluoroscopic images and the simulated fluoroscopic image corresponding to each imaging axis of the plurality of imaging axes, and calculates, as a treatment-couch motion amount by which the treatment-couch is to be moved, a motion amount from an intersection of the plurality of imaging axes to a midpoint of a common perpendicular of correction axes.

2. The positioning device according to claim 1, wherein the calculation processing part further obtains, as the correction axis, an axis connecting a position, where the intersection of the plurality of imaging axes is moved by the deviation amount, to the light source, for each of the plurality of imaging axes.

3. The positioning device according to claim 1, wherein the calculation processing part further calculates the deviation amount based on a position of a peak of a phase-only correlation function calculated from the fluoroscopic image and the simulated fluoroscopic image.

4. The positioning device according to claim 3, wherein the calculation processing part further calculates the phase-only correlation function from a region of interest set on the fluoroscopic image and the simulated fluoroscopic image.

5. The positioning device according to claim 1, wherein, in a case where a length of the common perpendicular is equal to or greater than a threshold value, the calculation processing part changes at least one of the fluoroscopic image and the simulated fluoroscopic image to redetermine the correction axis.

6. The positioning device according to claim 5, wherein the calculation processing part changes at least one of the fluoroscopic image and the simulated fluoroscopic image by performing predetermined image processing on at least one of the fluoroscopic image and the simulated fluoroscopic image.

7. The positioning device according to claim 1, wherein the calculation processing part further calculates motion amounts in a translation direction and a rotation direction of the treatment-couch based on a similarity between each corrected simulated fluoroscopic image obtained by correcting each simulated fluoroscopic image based on the treatment-couch motion amount, and each fluoroscopic image of the plurality of fluoroscopic images.

8. A radiotherapy device, comprising:

the positioning device according to claim 1;

a treatment-couch control system that moves the treatment-couch based on the treatment-couch motion amount calculated by the calculation processing part; and an irradiation device that uses radiation to irradiate a subject mounted on the moved treatment-couch.

9. A positioning method using a positioning device that controls a position of a treatment-couch on which a subject is mounted, the positioning method comprising:

acquiring a plurality of fluoroscopic images obtained by imaging the subject by receiving, on a detection surface via the subject, light from a light source for each of a plurality of imaging axes;

creating, for each of the plurality of imaging axes, a simulated fluoroscopic image obtained by projecting a three-dimensional fluoroscopic image of the subject onto the detection surface with respect to each imaging axis of the plurality of imaging axes; and obtaining, for each of the plurality of imaging axes, a correction axis obtained by correcting each imaging axis of the plurality of imaging axes based on a deviation amount between a fluoroscopic image of the plurality of fluoroscopic images and the simulated fluoroscopic image corresponding to each imaging axis of the plurality of imaging axes, and calculating, as a treatment-couch motion amount by which the treatment-couch is to be moved, a motion amount from an intersection of the plurality of imaging axes to a midpoint of a common perpendicular of correction axes.

* * * * *